United States Patent
Tokoshima et al.

(10) Patent No.: US 8,783,095 B2
(45) Date of Patent: Jul. 22, 2014

(54) ULTRAPURE WATER PRODUCTION FACILITY AND METHOD OF MONITORING ULTRAPURE WATER

(75) Inventors: Hiroto Tokoshima, Tokyo (JP); Hideki Kobayashi, Tokyo (JP)

(73) Assignee: Kurita Water Industries, Ltd., Tokyo (JP)

( * ) Notice: Subject to any disclaimer, the term of this patent is extended or adjusted under 35 U.S.C. 154(b) by 341 days.

(21) Appl. No.: 13/138,656

(22) PCT Filed: Mar. 29, 2010

(86) PCT No.: PCT/JP2010/055549
§ 371 (c)(1),
(2), (4) Date: Nov. 15, 2011

(87) PCT Pub. No.: WO2010/113861
PCT Pub. Date: Oct. 7, 2010

(65) Prior Publication Data
US 2012/0055556 A1  Mar. 8, 2012

(30) Foreign Application Priority Data
Mar. 31, 2009 (JP) ................................. 2009-086344

(51) Int. Cl.
*C02F 1/00* (2006.01)
*G01N 33/18* (2006.01)

(52) U.S. Cl.
USPC .......................................... 73/61.41; 210/85

(58) Field of Classification Search
USPC ....................................................... 73/61.41
See application file for complete search history.

(56) References Cited

U.S. PATENT DOCUMENTS

| | | | | |
|---|---|---|---|---|
| 4,670,137 A | * | 6/1987 | Koseki et al. | 210/96.1 |
| 5,487,981 A | * | 1/1996 | Nivens et al. | 435/30 |
| 6,310,017 B1 | * | 10/2001 | Grant et al. | 510/175 |
| 6,454,947 B1 | * | 9/2002 | Safir et al. | 506/12 |
| 8,035,799 B2 | * | 10/2011 | Kida | 355/53 |
| 8,525,971 B2 | * | 9/2013 | Shiraishi | 355/30 |

(Continued)

FOREIGN PATENT DOCUMENTS

| | | |
|---|---|---|
| CN | 2332720 Y | 8/1999 |
| JP | S62-159042 | 7/1987 |

(Continued)

OTHER PUBLICATIONS

English Translation of JP H5-138196.*

*Primary Examiner* — Hezron E Williams
*Assistant Examiner* — Alexander Mercado
(74) *Attorney, Agent, or Firm* — Manabu Kanesaka

(57) ABSTRACT

An ultrapure water production facility and a method of monitoring ultrapure water include an ultrapure water production system, a first monitoring unit including a resistivity meter, a second monitoring unit including a dissolved gas concentration meter, a TOC meter, a hydrogen peroxide concentration meter, a silica meter, a boron meter, an evaporation residue meter, and a water temperature meter connected in parallel, and a third monitoring unit including a particle meter. The third monitoring unit is provided in parallel with the first monitoring unit and the first monitoring unit and the second monitoring unit are connected in series.

8 Claims, 2 Drawing Sheets

(56) References Cited

U.S. PATENT DOCUMENTS

| | | | |
|---|---|---|---|
| 2002/0179508 A1* | 12/2002 | Nachtman et al. | 210/136 |
| 2007/0291239 A1* | 12/2007 | Shiraishi | 355/30 |
| 2008/0239260 A1* | 10/2008 | Shiraishi | 355/30 |
| 2008/0245738 A1* | 10/2008 | Coulter | 210/650 |
| 2010/0032387 A1* | 2/2010 | Yokoi | 210/797 |
| 2011/0210267 A1* | 9/2011 | Coulter | 250/435 |
| 2012/0026475 A1* | 2/2012 | Kida | 355/30 |
| 2013/0269425 A1* | 10/2013 | Rajagopalan et al. | 73/61.72 |

FOREIGN PATENT DOCUMENTS

| | | |
|---|---|---|
| JP | H04-027856 | 1/1992 |
| JP | H05-138196 | 6/1993 |
| JP | H05-293468 | 11/1993 |
| JP | H06-194298 | 7/1994 |
| JP | H07-284755 | 10/1995 |

* cited by examiner

ULTRAPURE WATER PRODUCTION FACILITY AND METHOD OF MONITORING ULTRAPURE WATER

FIELD OF INVENTION

The present invention relates to an ultrapure water production facility including a monitoring system for monitoring the quality of ultrapure water produced in an ultrapure water production system and supplied to a use point, and to a method of monitoring the ultrapure water.

BACKGROUND ART

Ultrapure water has a wide variety of uses, such as cleaning electronic components and surface treatment. In recent years, demands for a small amount of high-purity ultrapure water to be used as cleaning water or water for immersion exposure have been increasing.

Typically, when high-purity ultrapure water is supplied to a use point, the quality of ultrapure water to be supplied is monitored from various aspects using multiple on-line measuring instruments so that whether or not the purity is maintained can be constantly monitored. Examples of the measuring instruments used at this time include a resistivity meter, a particle meter, a dissolved gas concentration meter, a TOC meter, a hydrogen peroxide concentration meter, a silica meter, a boron meter, an evaporation residue meter, and a water temperature meter. The measuring instruments are selected depending on monitoring items required for its use (for example, see Patent Document 1).

FIG. 2 is a system diagram showing a conventional ultrapure water production facility provided with a plurality of measuring instruments for monitoring the water quality. Raw water (for example, primary pure water) introduced from a pipe 10 is supplied to an ultrapure water production system 2 via a storage tank 1 and a pipe 11, is raised in pressure by a pump in the ultrapure water production system 2, and is treated by various polishing-up mechanisms (such as TOC removal, degassing, dissolved ion removal, and particle removal). Thus, ultrapure water is produced. The ultrapure water produced in the ultrapure water production system 2 is supplied to a use point 3 through an ultrapure water supply pipe 12 to be used. At this time, in order to maintain the purity of the ultrapure water, a circulation system is formed in which an amount of ultrapure water larger than the amount used in the use, point 3 is supplied, and unused ultrapure water is returned to the storage tank 1 through an ultrapure water return pipe 14 to be reused as the raw water.

A portion of the ultrapure water supplied from the ultrapure water production system 2 to the use point 3 is extracted by a monitoring water extracting pipe 13 branching off from the pipe 12 and is introduced into the respective measuring instruments arranged in parallel (in FIG. 2, a particle meter A, a resistivity meter B, a boron meter C, a DO/DN (dissolved oxygen/dissolved nitrogen) meter D, a silica meter E, a TOC meter F, an $H_2O_2$ (hydrogen peroxide) meter G, and an evaporation residue meter H), where predetermined water quality items are measured. The monitoring wastewater after the measurement is discharged from the respective measuring instruments A to H to the outside of the system through a monitoring wastewater discharging pipe 15.

As shown in FIG. 2, the quality of ultrapure water is independently measured by these measuring instruments. Therefore, ultrapure water, serving as monitoring water, is introduced from the extracting pipe 13 into the respective measuring instruments, and the monitoring wastewater after the measurement is discharged from the respective measuring instruments.

The amount of monitoring water required by each of these measuring instruments for measurement is only several tens to several hundreds mL/min. However, the larger the number of monitoring items, in other words, the more the high-purity ultrapure water is required, the larger the number of monitoring measuring instruments. As a result, the total amount of monitoring water required for water quality monitoring increases. Therefore, in the case where a small amount of high-purity ultrapure water is used, the amount of monitoring water can be larger than the amount of ultrapure water supplied to the use point. In such a case, in order to ensure the amount of monitoring water, the ultrapure water production system needs to be made larger than required for the primary use. This has lead to an increase in the system cost.

LIST OF DOCUMENT

Patent Document

Patent Document 1: Japanese Patent Publication 5-138196A

OBJECT OF INVENTION

An object of the present invention is to provide an ultrapure water production facility in which the size of an ultrapure water production system is reduced, thereby reducing the system cost, by solving the above-described conventional problems to reduce the amount of monitoring water required when the quality of ultrapure water is measured and monitored using a plurality of measuring instruments, and to provide a method of monitoring the ultrapure water.

SUMMARY OF INVENTION

An ultrapure water production facility according to a first aspect comprises an ultrapure water production system; a supply pipe for supplying ultrapure water produced in the ultrapure water production system to a use point; and a monitoring system for monitoring the quality of the ultrapure water extracted from the supply pipe. The monitoring system includes two or more stages of different types of water quality measuring devices connected in series.

The ultrapure water production facility according to a second aspect is characterized in that, in the first aspect, the monitoring system comprises first monitoring means including a resistivity meter; second monitoring means in which one type or two or more types of measuring instruments, selected from a group consisting of a dissolved gas concentration meter, a TOC meter, a hydrogen peroxide concentration meter, a silica meter, a boron meter, an evaporation residue meter, and a water temperature meter, are connected in parallel; a transportation pipe for introducing a portion of monitoring wastewater discharged from the first monitoring means into the second monitoring means; and a discharging pipe for discharging the remaining of the monitoring wastewater.

The ultrapure water production facility according to a third aspect is characterized in that, in the second aspect, the monitoring system further comprises third monitoring means including a particle meter, the third monitoring means being provided in parallel with the first monitoring means.

The ultrapure water production facility according to a fourth aspect is characterized in that, in the second or third aspect, it further comprises a circulation pipe for circulating the monitoring wastewater discharged from the discharging pipe as raw water of the ultrapure water production system.

A method of monitoring ultrapure water ultrapure water in which a portion of ultrapure water supplied from a production system to a use point is separated and the water quality thereof is monitored, according to a fifth aspect, is characterized in that the separated ultrapure water is allowed to pass through a monitoring system consisting two or more stages of different types of water quality measuring devices connected in series so that the water quality is monitored.

A method of monitoring ultrapure water according to a sixth aspect is characterized in that, in the fifth aspect, the monitoring system comprises first monitoring means including a resistivity meter; second monitoring means in which one type or two or more types of measuring instruments, selected from a group consisting of a dissolved gas concentration meter, a TOC meter, a hydrogen peroxide concentration meter, a silica meter, a boron meter, an evaporation residue meter, and a water temperature meter, are connected in parallel; a transportation pipe for introducing a portion of monitoring wastewater discharged from the first monitoring means into the second monitoring means; and a discharging pipe for discharging the remaining of the monitoring wastewater.

The method of monitoring ultrapure water according to a seventh aspect is characterized in that, in the sixth aspect, the monitoring system further comprises third monitoring means including a particle meter, the third monitoring means being provided in parallel with the first monitoring means.

The method of monitoring ultrapure water according to an eighth aspect is characterized in that, in the sixth or seventh aspect, the monitoring wastewater discharged from the discharging pipe is circulated and used as raw water of the ultrapure water production system.

ADVANTAGEOUS EFFECTS OF INVENTION

In the present invention, ultrapure water extracted from the supply pipe extending from the ultrapure water production system to the use point is allowed to pass, in series, through two or more stages of different types of water quality measuring devices connected in series. By making these measuring instruments use the same monitoring water, which is required for measuring the water quality, the amount of monitoring water can be reduced. As a result, the size of the ultrapure water production system can be reduced, and hence, the system cost can be reduced.

It is preferable that this monitoring system comprise first monitoring means including a resistivity meter; second monitoring means in which one type or two or more types of measuring instruments, selected from a group consisting of a dissolved gas concentration meter, a TOC meter, a hydrogen peroxide concentration meter, a silica meter, a boron meter, an evaporation residue meter, and a water temperature meter, are connected in parallel; a transportation pipe for introducing a portion of monitoring wastewater discharged from the first monitoring means into the second monitoring means; and a discharging pipe for discharging the remaining of the monitoring wastewater (the second and sixth aspects).

That is, the resistivity meter requires a relatively large amount of monitoring water for measuring the water quality, and, even if the water quality is measured with the resistivity meter, the influence on the quality of the monitoring wastewater is insignificant. Furthermore, the measuring instruments, such as the dissolved gas concentration meter, the TOC meter, the hydrogen peroxide concentration meter, the silica meter, the boron meter, the evaporation residue meter, and the water temperature meter, can perform stable measurement using the monitoring wastewater discharged from the resistivity meter and require a small amount of monitoring water for the measurement, compared with the resistivity meter. Therefore, it is effective to provide the resistivity meter on the upstream side and dispose the measuring instruments in parallel on the downstream side of the resistivity meter, so that the monitoring wastewater discharged from the resistivity meter is divided and supplied to the respective measuring instruments and so that the excess monitoring wastewater is discharged therefrom, thereby stabilizing the measurement values of the respective measuring instruments and reducing the amount of monitoring water.

On the other hand, to stabilize the measurement value, it is preferable that the particle meter be provided independently. Accordingly, it is preferable that the third monitoring means, including the particle meter, be provided in parallel with the first monitoring means, including the resistivity meter (the third and seventh aspects).

In the monitoring system of the present invention, the monitoring wastewater discharged from the first monitoring means, including the resistivity meter, is highly pure. Therefore, it is preferable that, in this monitoring wastewater, excess monitoring wastewater that is not supplied to the second monitoring means be circulated and used as the raw water of ultrapure water (the fourth and eighth aspects).

DESCRIPTION OF EMBODIMENTS

Figure 1:
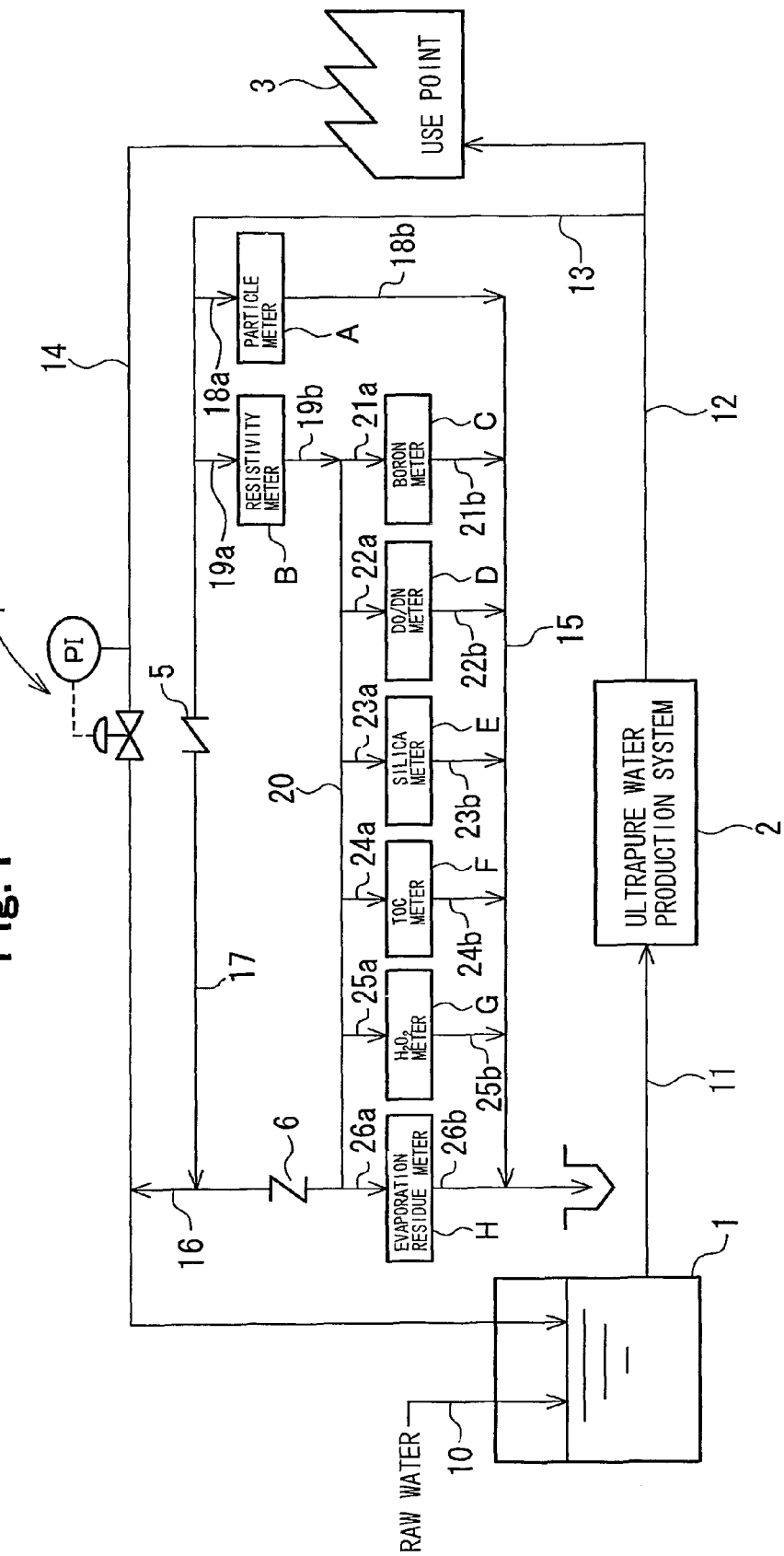
FIG. 1 is a system diagram showing an embodiment of an ultrapure water production facility of the present invention.

Referring to the drawings, embodiments of the present invention will be described in detail below.

FIG. 1 is a system diagram showing an embodiment of an ultrapure water production facility of the present invention. In FIG. 1, components having the same function as those shown in FIG. 2 are denoted by the same reference numerals.

Figure 2:
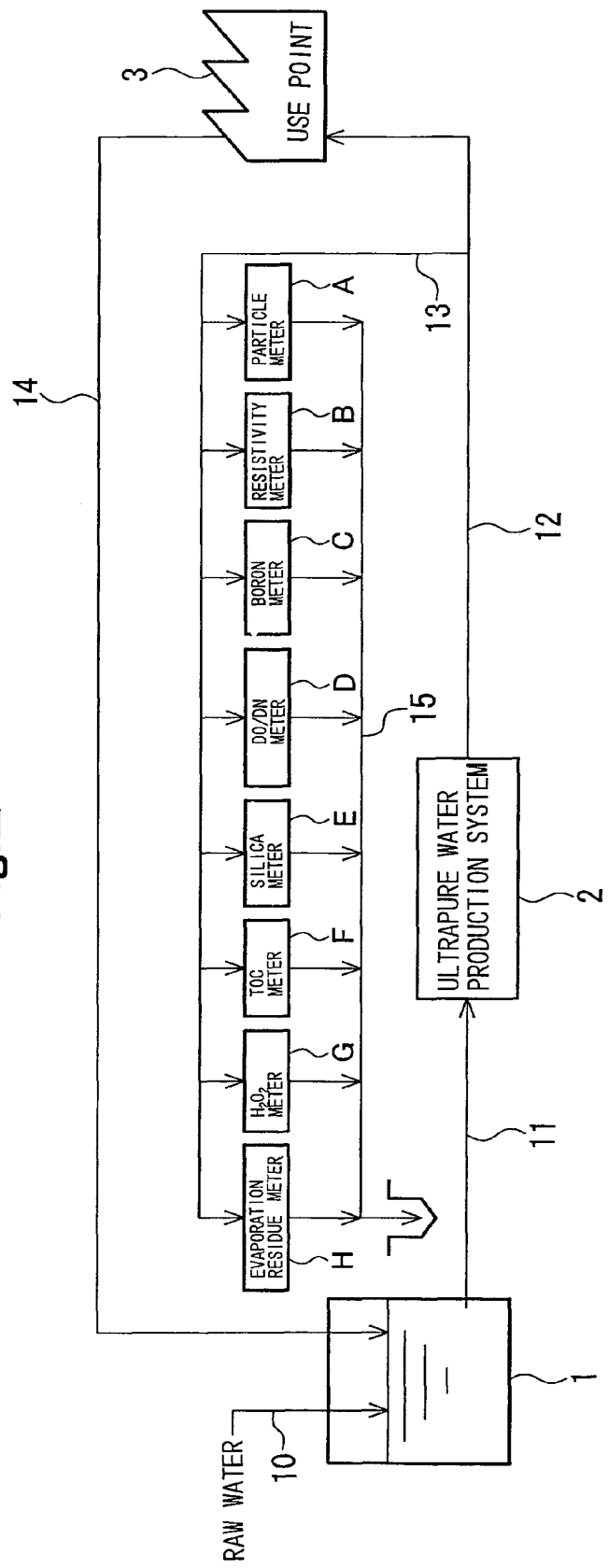
FIG. 2 is a system diagram showing a conventional ultrapure water production facility.

In the ultrapure water production facility in FIG. 1, similarly to FIG. 2, the raw water of ultrapure water from a pipe 10 is introduced into an ultrapure water production system 2 via a storage tank 1 and a pipe 11, is raised in pressure by a pump in the ultrapure water production system 2, and is treated by various polishing-up mechanisms (such as TOC removal, degassing, dissolved ion removal, and particle removal). Thus, ultrapure water is produced. The ultrapure water produced in the ultrapure water production system 2 is supplied through an ultrapure water supply pipe 12 to a use point 3 to be used, and excess ultrapure water that is not used in the use point 3 is returned to the storage tank 1 through an ultrapure water return pipe 14 to be reused as the raw water. Note that the reference numeral 4 represents an ultrapure-water pressure adjusting mechanism, which performs pressure control such that the water pressure is constant, even when the amount of water used in the use point 3 is varied, causing variation in the amount of water flowing through the return pipes 14 and 15 extending from the use point 3 to the storage tank 1. The water-pressure adjusting mechanism 4 may be of any type, as long as it does not change the water quality of returning ultrapure water, making it unsuitable as the raw water of ultrapure water.

In the ultrapure water production facility in FIG. 1, a particle meter (third monitoring means) A and a resistivity meter (first monitoring means) B, which form a monitoring system, are provided in parallel, and a measuring instrument group serving as second monitoring means, in which a boron meter C, a DO/DN meter D, a silica meter E, a TOC meter F, a $H_2O_2$ meter G, and an evaporation residue meter H are arranged in parallel, is disposed on the downstream side of the resistivity meter B so as to be connected in series thereto.

Thus, ultrapure water (monitoring water) separated by a monitoring water extracting pipe 13 branching off from the pipe 12 that supplies ultrapure water from the ultrapure water production system 2 to the use point 3 is introduced into the particle meter A and the resistivity meter B via a pipe 18a and a pipe 19a, respectively, and is subjected to the measurement of the number of particles and the specific resistance. The monitoring wastewater discharged from the particle meter A is discharged outside the system through a pipe 18b and a pipe 15.

On the other hand, the monitoring wastewater discharged from the resistivity meter B is supplied to the measuring instruments constituting the second monitoring means through a pipe 19b and a pipe 20. That is, the monitoring wastewater is introduced into the boron meter C, the DO/DN meter D, the silica meter E, the TOC meter F, the $H_2O_2$ meter G, and the evaporation residue meter H through a pipe 21a, pipe 22a, a pipe 23a, a pipe 24a, a pipe 25a, and a pipe 26a, respectively, and is subjected to the measurement of the boron concentration, the DO concentration and DN concentration, the silica concentration, the TOC concentration, the $H_2O_2$ concentration, and the amount of evaporation residue in the measuring instruments C to H, respectively. The monitoring wastewater discharged from the measuring instruments C to H flows through a pipe 21b, a pipe 22b, a pipe 23b, a pipe 24b, a pipe 25b, and a pipe 26b, via the pipe 15, and is discharged outside the system.

As has been described above, the resistivity meter B requires a relatively large amount of monitoring water to obtain a stable measurement value, and other measuring instruments require a small amount of monitoring water. Therefore, as shown in FIG. 1, it is preferable that the resistivity meter B, serving as the first monitoring means, be disposed on the upstream side, and the other measuring instruments, serving as the second monitoring means, be arranged in parallel on the downstream side of the resistivity meter B. However, if the particle meter A is disposed on the downstream side of the first monitoring means, such as the resistivity meter B, the measurement value thereof may be unstable because of mixing of particles from the inner wall surface of the measuring instrument on the upstream side. Thus, it is preferable that the particle meter A be arranged separately from and in parallel with the resistivity meter B and that ultrapure water from the monitoring water extracting pipe 13 be directly introduced into each of the particle meter A and the resistivity meter B. Although the particle meter A is not specifically limited, typically, a laser-scattering particle meter is appropriately used.

In FIG. 1, the main pipe 20 for supplying monitoring wastewater from the resistivity meter B to the respective measuring instruments C to H of the second monitoring means has a discharging pipe 16, through which excess water of the monitoring wastewater from the resistivity meter B, which is not supplied to the respective measuring instruments C to H of the second monitoring means, is discharged outside the monitoring system. This discharging pipe 16 is connected to the return pipe 14 for the ultrapure water. The excess monitoring wastewater is returned to the storage tank 1 through the pipes 16 and 14, so that it can be circulated and reused as the raw water of ultrapure water. That is, because the purity of the monitoring wastewater from the resistivity meter B is high enough, the monitoring wastewater can be reused as the raw water of ultrapure water, thereby reducing the amount of the raw water.

Furthermore, in FIG. 1, excess ultrapure water extracted by the monitoring water extracting pipe 13 but not supplied to the particle meter A or the resistivity meter B also flows through the pipes 17, 16, and 14 and is returned to the storage tank 1, where it is reused as the raw water of ultrapure water.

Note that the reference numerals 5 and 6 represent check valves for preventing backflow. Any type of check valve may be used as the check valves 5 and 6, as long as they do not change the quality of water flowing through the pipes, making the water unsuitable as the raw water of ultrapure water.

Although the amounts of monitoring water supplied to the respective measuring instruments, constituting the monitoring system, vary depending on the specifications of the measuring instruments used, it is preferable that the amounts of monitoring water be set, for example, as follows to obtain stable measurement values.

particle meter A: 0.5 L/min or more, for example, 0.5 to 0.8 L/min resistivity meter B: 1 L/min or more, for example, 1 to 2 L/min boron meter C: 0.1 L/min or more, for example, 0.1 to 0.5 L/min DO/DN meter D: 0.3 L/min or more, for example, 0.3 to 0.5 L/min silica meter E: 0.1 L/min or more, for example, 0.1 to 0.5 L/min TOC meter F: 0.1 L/min or more, for example, 0.1 to 0.3 L/min $H_2O_2$ meter G: 0.2 L/min or more, for example, 0.2 to 0.5 L/min evaporation residue meter H: 0.1 L/min or more, for example, 0.1 to 0.5 L/min Furthermore, by adjusting the amount of water such that, in the monitoring wastewater from the resistivity meter B, excess monitoring wastewater returned to the storage tank 1 through the pipes 16 and 14 without being supplied to the respective measuring instruments C to H of the second monitoring means is about 0.1 to 1 L/min, even when a batch-type monitor is used, variation in water pressure in a header pipe can be reduced, and variation in water pressure in other monitors can be reduced, making it possible to perform stable monitoring. The amount of excess monitoring wastewater can be adjusted by controlling the amount of water at the inlet side and/or outlet side of the resistivity meter B.

Note that the smaller the amount of ultrapure water extracted by the monitoring water extracting pipe 13 and returned to the storage tank 1 through the pipes 17, 16, and 14, without being supplied to the particle meter A and the resistivity meter B, the more preferable for a reduction in the amount of monitoring water, and a preferable amount of ultrapure water is, typically, 0.3 L/min or less, more specifically, from 0 to 0.1 L/min.

FIG. 1 shows an example of an ultrapure water production facility according to an embodiment of the present invention. The present invention is not limited to the illustrated embodiment, as long as it does not depart from the spirit thereof.

For example, there is no need to provide all the illustrated measuring instruments C to H, serving as the second monitoring means. Depending on the water quality items to be monitored, some of them may be provided. Furthermore, in addition to the illustrated measuring instruments C to H, measuring instruments, such as a water temperature meter, a metal monitor, and a dissolved gas concentration meter other than the DO meter or DN meter, serving as the second monitoring means, may be provided. Furthermore, although the DO meter and the DN meter are accommodated in a single measuring instrument in FIG. 1, they may be provided as separate measuring instruments. In that case, the DO meter and the DN meter may be arranged in series. Furthermore, in FIG. 1, the particle meter A is provided in a pipe branching off from the monitoring water extracting pipe 13 on the upstream side of the resistivity meter B. However, the positions of the particle meter A and the resistivity meter B is not limited to this, and the resistivity meter B may be provided in a pipe branching off on the upstream side of the particle meter A. Furthermore, when the purity of the monitoring wastewater discharged through the pipe 15 is high, the wastewater may also be returned to the storage tank 1 to be circulated and used as the raw water of ultrapure water.

Note that, although not shown, the values measured by the respective measuring instruments are input to a control unit, and the quality of the ultrapure water is monitored on the basis of the measured values.

With this ultrapure water production facility, it is possible to supply ultrapure water while constantly monitoring the quality of the ultrapure water supplied from the ultrapure water production system 2 to the use point 3, and, by reducing the amount of monitoring water at this time, the ultrapure water production system 2 may have a size corresponding to the amount of water used at the use point 3, not the amount of monitoring water. Thus, the system cost can be reduced.

EXAMPLES

The present invention will be described in more detail below, with reference to Example and Comparative Example.

Note that, in the following Example and Comparative Example, measuring instruments listed below were used to measure the quality of ultrapure water.

Particle meter: "KLAMIC-KS" manufactured by Kurita Water Industries Ltd.

Resistivity meter: "MX-4" manufactured by Kurita Water Industries Ltd.

TOC meter: "ANATEL A-1000-XP" manufactured by HachUltra Co., Ltd.

DO/DN meter: "ORBISPHERE Model 3620" manufactured by HachUltra Co., Ltd.

Comparative Example 1

Ultrapure water was monitored with the conventional ultrapure water production facility shown in FIG. 2 (note that only the particle meter A, the resistivity meter B, the DO/DN meter D, and the TOC meter F were used as the measuring instruments for measuring the water quality, while the boron meter C, the silica meter E, the $H_2O_2$ meter G, and the evaporation residue meter H were omitted).

The amounts of monitoring water supplied to the respective measuring instruments were as follows.

Particle meter A: 0.5 L/min
Resistivity meter B: 1.5 L/min
DO/DN meter D: 0.3 L/min
TOC meter F: 0.2 L/min Therefore, it was necessary to separate a 2.5 (=0.5+1.5+0.3+0.2) L/min of ultrapure water, serving as monitoring water, from the supply pipe 12 through which ultrapure water is supplied from the ultrapure water production system to the use point 3, via the pipe 13.

Example 1

Ultrapure water was monitored with the ultrapure water production facility of the present invention shown in FIG. 1 (note that only the particle meter A, the resistivity meter B, the DO/DN meter D, and the TOC meter F were used as the measuring instruments for measuring water quality, while the boron meter C, the silica meter E, the $H_2O_2$ meter G, and the evaporation residue meter H were omitted).

The amounts of monitoring water supplied to the respective measuring instruments were the same as those in Comparative Example 1, which are as follows.

Particle meter A: 0.5 L/min
Resistivity meter B: 1.5 L/min
DO/DN meter D: 0.3 L/min
TOC meter F: 0.2 L/min In 1.5 L/min of monitoring wastewater from the resistivity meter B, 1.0 (=1.5−0.2−0.3) L/min of excess water not supplied to the DO/DN meter D or the TOC meter F was circulated through the pipes 16 and 14 back to the storage tank 1.

As a result, only 2.0 (=0.5+1.5) L/min of ultrapure water was needed to be extracted from the supply pipe 12 via the pipe 13 for monitoring, and thus, the required amount of monitoring water was reduced as much as by 20%. Thus, the ultrapure water production system 2 can be reduced in size by an amount corresponding to the reduction.

Furthermore, by reusing 1.0 L/min of monitoring water out of 2.0 L/min as the raw water of ultrapure water, the amount of raw water was reduced.

Note that there were no differences at all between the water quality measurement values obtained by the measuring instruments used in Comparative Example 1 and the water quality measurement values obtained by the measuring instruments used in Example 1, and it was confirmed that, as in Example 1, even when the wastewater from the resistivity meter was introduced into the DO/DN meter and the TOC meter to measure the water quality, stable monitoring was possible.

Although the present invention has been described in detail using a specific aspect, it is obvious to those skilled in the art that various modifications can be made without departing from the spirit and scope of the present invention.

This application is based on a Japanese patent application filed on Mar. 31, 2009 (Japanese patent application 2009-086344), and the entirety of which is hereby incorporated by reference.

The invention claimed is:

1. An ultrapure water production facility, comprising:
an ultrapure water production system;
a supply pipe for supplying ultrapure water produced in the ultrapure water production system to a use point; and
a monitoring system for monitoring a quality of the ultrapure water extracted from the supply pipe, comprising
a first monitoring unit including a resistivity meter,
a second monitoring unit in which one type or two or more types of measuring instrument, selected from the group consisting of a dissolved gas concentration meter, a TOC meter, a hydrogen peroxide concentration meter, a silica meter, a boron meter, an evaporation residue meter, and a water temperature meter, are connected in parallel,
a third monitoring unit including a particle meter, the third monitoring unit being provided in parallel with the first monitoring unit and the second monitoring unit,
a transportation pipe for introducing a portion of monitoring wastewater discharged from the first monitoring unit into the second monitoring unit, and
a discharging pipe for discharging the remaining of the monitoring wastewater, wherein the first monitoring unit and the second monitoring unit are connected in series.

2. The ultrapure water production facility according to claim 1, further comprising a circulation pipe for circulating the monitoring wastewater discharged from the discharging pipe as raw water through the ultrapure water production system.

3. A method of monitoring ultrapure water in which a portion of ultrapure water supplied from a production system to a use point is separated and a water quality thereof is monitored, wherein the separated ultrapure water is allowed to pass through a monitoring system comprising a first monitoring unit including a resistivity meter, a second monitoring unit in which one type or two or more types of measuring instruments, selected from the group consisting of a dissolved gas concentration meter, a TOC meter, a hydrogen peroxide concentration meter, a silica meter, a boron meter, an evaporation residue meter, and a water temperature meter, are connected in parallel, a third monitoring unit including a particle meter, the third monitoring unit being provided in parallel with the first monitoring unit and the second monitoring unit, a transportation pipe for introducing a portion of monitoring wastewater discharged from the first monitoring unit into the second monitoring unit, and a discharging pipe for discharging the remaining of the monitoring wastewater, and the first monitoring unit and the second monitoring unit are connected in series so that the water quality is monitored.

4. The method of monitoring ultrapure water according to claim 3, wherein the monitoring wastewater discharged from the discharging pipe is circulated and used as raw water through the ultrapure water production system.

5. An ultrapure water production facility, comprising:

an ultrapure water production system producing an ultrapure water;

a use point where the ultrapure water is used for a predetermined usage;

a supply pipe supplying the ultrapure water to the use point from the ultrapure water production system;

a first monitoring unit including a resistivity meter;

a second monitoring unit in which at least one measuring instrument selected from the group consisting of a dissolved gas concentration meter, a TOC meter, a hydrogen peroxide concentration meter, a silica meter, a boron meter, an evaporation residue meter, and a water temperature meter is connected in parallel, the second monitoring unit being provided in series with the first monitoring unit;

a third monitoring unit including a particle meter, the third monitoring unit being provided in parallel with the first monitoring unit and the second monitoring unit;

an extracting pipe branching off from the supply pipe, separating a monitoring water from the ultrapure water, and supplying the monitoring water to the first monitoring unit and third monitoring unit;

a transportation pipe introducing a portion of the monitoring water discharged from the first monitoring unit into the second monitoring unit; and a discharging pipe discharging a remaining of the monitoring water not introduced to the second monitoring unit, to the ultrapure water production system.

6. The ultrapure water production facility according to claim 5, further comprising another discharging pipe discharging the monitoring water discharged from the second monitoring unit to an outside of the ultrapure water production system.

7. The ultrapure water production facility according to claim 6, wherein, in the second monitoring unit, the dissolved gas concentration meter, the TOC meter, the hydrogen peroxide concentration meter, the silica meter, the boron meter, the evaporation residue meter, and the water temperature meter are arranged in parallel.

8. The ultrapure water production facility according to claim 6, wherein the monitoring water supplied to the third monitoring unit is discharged from the another discharging pipe.

* * * * *